United States Patent [19]
Geller et al.

[11] Patent Number: 5,501,979
[45] Date of Patent: Mar. 26, 1996

[54] HERPES SIMPLEX VIRUS TYPE I EXPRESSION VECTOR

[75] Inventors: Alfred I. Geller, Jamaica Plains; Xandra O. Breakefield, Newton, both of Mass.

[73] Assignee: The General Hospital Corporation, Charlestown, Mass.

[21] Appl. No.: 159,110

[22] Filed: Nov. 30, 1993

Related U.S. Application Data

[63] Continuation of Ser. No. 913,977, Jul. 16, 1992, abandoned, which is a continuation of Ser. No. 304,619, Feb. 1, 1989, abandoned.

[51] Int. Cl.$^6$ .......................... C12N 15/86; C12N 15/63
[52] U.S. Cl. ............................. 435/320.1; 435/172.1; 435/172.3
[58] Field of Search .................. 435/69.1, 172.1, 435/172.3, 235.1, 320.1

[56] References Cited

U.S. PATENT DOCUMENTS 5,288,641  2/1994  Roizman et al. ................. 435/320.1

FOREIGN PATENT DOCUMENTS 0453242  10/1991  European Pat. Off. .
WO90/09441  8/1990  WIPO .

OTHER PUBLICATIONS

Sabel et al., *Society for Neuroscience Abstracts* 15:9 (1989).
Federoff et al., *Proc. Natl. Acad. Sci. USA* 89:1636–1640 (1992).
During et al., *Science* 266:1399–1403 (1994).
Suhar et al., *American Society for Microbiology Abstracts of the Annual Meeting*, 286 (1985).
Marchioli et al., *American Society for Microbiology Abstracts of the Annual Meeting*, 286 (1985).
Yan et al., *American Society for Microbiology Abstracts of the Annual Meeting*, 286 (1985).
Bear et al. *Journal of Molecular and Applied, Genetics*, 2:471–484 (1984).
Matz et al., *Journal of General Virology*, 64:2261–2270 (1983).
Geller et al., "Defective HSV-1 Vector Expresses *Escherichia coli* β–Galactosidase in Cultured Peripheral Neurons," *Science* 241:1667–1669 (Sep. 23, 1988).
Gerdes et al., "Acute Infection of Differentiated Neuroblastoma Cells by Latency–Positive and Latency–Negative Herpes Simplex Virus *ts* Mutants," *Virology* 94:430–441 (1979).
Marchioli et al., "Use of Recombinant Herpes Simplex Virus Type 1 as an Expression Vector to Induce Immunity to the Major Excreted Glycoprotein of Pseudorabies Virus," *Abstracts of the Annual Meeting of the American Society for Microbiology*:286, Abstract No. S 28 (1985).
Palella et al., "Herpes Simplex Virus–Mediated Human Hypoxanthine–Guanine Phopshoribosyltransferase Gene Transfer into Neuronal Cells," *Mol. and Cell. Biol.* (1):457–460 (Jan. 1988).
Robbins et al., "Construction of *E. coli* Expression Plasmid Libraries: Localization of a Pseudorabies Virus Glycoprotein Gene," *J. Mol. Appl. Genet.* 2:485–496 (1984).
Shih et al., "Herpes Simplex Virus as a Vector for Eukaryotic Viral Genes," in Lerner, R. A. et al., eds. *Vaccines 85*, Cold Spring Harbor Laboratory, pp. 177–180 (1985).
Watson et al., "Latency Competence of Thirteen HSV-1 Temperature–sensitive Mutants," *J. Gen. Virol.* 49:149–159 (1980).

(List continued on next page.)

Primary Examiner—Mindy Fleisher
Assistant Examiner—David Guzo
Attorney, Agent, or Firm—Sterne, Kessler, Goldstein & Fox

[57] ABSTRACT

A recombinant HSV-1 vector capable of infecting and being propagated in a non-mitotic cell. The vector can be used to treat neurological diseases, and to produce animal and in vitro models of such diseases.

13 Claims, 1 Drawing Sheet

OTHER PUBLICATIONS

Arvidson, B., "Retrograde Transport of Horseradish Peroxidase In Sensory and Adrenergic Neurons Following Injection into the Anterior Eye Chamber," *J. Neurocytol.* 8:751–764 (1979).

Baccaglini et al., "Some rat sensory neurons in culture express characteristics of differentiated pain sensory cells," *Proc. Natl. Acad. Sci. USA* 80:594–598 (1983).

Baetge et al., "Transgenic mice express the human phenylethanolamine N–methyltransferase gene in adrenal medulla and retina," *Proc. Natl. Acad. Sci. USA* 85:3648–3652 (1988).

Bigotte et al., "Degeneration of Trigeminal Ganglion Neurons Caused by Retrograde Axonal Transport of Doxorubicin," *Neurology* 37:985–992 (1987).

Black et al., "Biochemistry of Information Storage In the Nervous System," *Science* 236:1263–1268 (1987).

Böhnlein et al., "Functional Analysis of the Regulatory Region of Polyoma Mutant F9–1 DNA," *Nucleic Acids Research* 13(13):4789–4809 (1985).

Breakefield et al., "Herpes Simplex Virus for Gene Delivery to Neurons," *The New Biologist* 3(3):203–218 (1991).

Cai et al., "Herpes Simplex Virus Type 1 ICP0 Plays a Critical Role In the De Novo Synthesis of Infectious Virus Following Transfection of Viral DNA," *J. Virol.* 63(11):4579–4589 (1989).

Coen et al., "Thymidine kinase–negative herpes simplex virus mutants establish latency in mouse trigeminal ganglia but do not reactivate," *Proc. Natl. Acad. Sci. USA* 86:4736–4740 (1989).

Colbere–Garapin et al., "Cloning of the active thymidine kinase gene of herpes simplex virus type 1 in *Escherichia coli* K–12," *Proc. Natl. Acad. Sci. USA* 76:3755–3759 (1979).

Cook et al., "Pathogenesis of Herpetic Neuritis and Ganglionitis In Mice: Evidence for Intra–Axonal Transport of Infection," *Infect. Immun.* 7(2):272–288 (1973).

Croen et al., "Latent Herpes Simplex Virus In Human Trigeminal Ganglia," *The New England J. of Med.* 317(23):1427–1432 (1987).

Davison et al., "Determination of the Sequence Alteration In the DNA of the Herpes Simplex Virus Type 1 Temperature––sensitive Mutant *ts* K," *J. Gen. Virol.* 65:859–863 (1984).

De Koninck et al., "Substance P–Mediated Slow Excitatory Postsynaptic Potential Elicited In Dorsal Horn Neurons In Vivo by Noxious Stimulation," *Proc. Natl. Acad. Sci. USA* 88:11344–11348 (1991).

Dobson et al., "A Latent, Nonpathogenic HSV–1–Derived Vector Stably Expresses β–Galactosidase In Mouse Neurons," *Neuron* 5:353–360 (1990).

Dobson et al., "Identification of the Latency–Associated Promoter by Expression of Rabbit Beta–Globin mRNA In Mouse Sensory Nerve Ganglia Latently Infected With a Recombinant Herpes Simplex Virus," *J. Virol.* 63(9):3844–3851 (1989).

Efstathiou et al., "Detection of Herpes Simplex Virus–Specific DNA Sequences In Latently Infected Mice and In Humans," *J. Virol.* 57(2):446–455 (1986).

Efstathiou et al., "The Role of Herpes Simplex Virus Type 1 Thymidine Kinase in Pathogenesis," *J. Gen. Virol.* 70:869–879 (1989).

Fenwick, M. L., "The Effects of Herpesviruses On Cellular Macromolecular Synthesis," *Compr. Virol.* 19:359–390 (1984).

Forss–Petter et al., "Transgenic Mice Expressing β–Galactosidase in Mature Neurons Under Neuron–Specific Enolase Promoter Control," *Neuron* 5:187–197 (1990).

Friedman, T., "Progress Toward Human Gene Therapy," *Science* 244:1275–1281 (1989).

Heilbronn et al., "A Subset of Herpes Simplex Virus Replication Genes Induces DNA Amplification Within the Host Cell Genome," *J. Virol.* 63(9):3683–3692 (1989).

Ho et al., "β–Galactosidase as a Marker In the Peripheral and Neural Tissues of the Herpes Simplex Virus–Infected Mouse," *Virology* 167:279–283 (1988).

Ho et al., "Herpes simplex virus latent RNA (LAT) is not required for latent infection in the mouse," *Proc. Natl. Acad. Sci. USA* 86:7596–7600 (1989).

Huang et al., "Introduction of a Foreign Gene (*Escherichia coli lacZ*) into Rat Neostriatal Neurons Using Herpes Simplex Virus Mutants: A Light and Electron Microscopic Study," *Exp. Neurol.* 115:303–315 (1992).

Javier et al., "A Herpes Simplex Virus Transcript Abundant in Latently Infected Neurons Is Dispensable for Establishment of the Latent State," *Virology* 166:254–257 (1988).

Javier et al., "Localization of a Herpes Simplex Virus Neurovirulence Gene Dissociated from High–Titer Virus Replication in the Brain," *J. Virol.* 62(4):1381–1387 (1988).

Koprowski, H., "Possible Role of Herpes Virus in the Chronic CNS Diseases," in *Persistent Viruses*, F. G. Stevens (ed.), Academic Press, N.Y., pp. 691–699 (1978).

Kosz–Vnenchak et al., "Restricted Expression of Herpes Simplex Virus Lytic Genes During Establishment of Latent Infection by Thymidine Kinase–Negative Mutant Viruses," *J. Virol.* 64(11):5396–5402 (1990).

Kuwayama et al., "A Quantitative Correlation of Substance P–, Calcitonin Gene–Related Peptide– and Cholecystokinin– Like Immunoreactivity with Retrogradely Labeled Trigeminal Ganglion Cells Innervating the Eye," *Brain Res.* 405:220–226 (1987).

Kuypers et al., "Viruses as Transneuronal Tracers," *TINS* 13(2):71–75 (1990).

Kwong et al., "The Herpes Simplex Virus Virion Host Shutoff Function," *J. Virol.* 63(11):4834–4839 (1989).

Leib et al., "A Deletion Mutant of the Latency–Associated Transcript of Herpes Simplex Virus Type 1 Reactivates from the Latent State with Reduced Frequency," *J. Virol.* 63(7):2893–2900 (1989).

Leib et al., "Immediate–Early Regulatory Gene Mutants Define Different Stages in the Establishment and Reactivation of Herpes Simplex Virus Latency," *J. Virol.* 63(2):759–768 (1989).

Leist et al., "Latent Infections in Spinal Ganglia with Thymidine Kinase–Deficient Herpes Simplex Virus," *J. Virol.* 63(11):4976–4978 (1989).

Longnecker et al., "Herpes Simplex Viruses as Vectors: Properties of a Prototype Vaccine Strain Suitable for Use as a Vector," in *Viral Vectors*, Gluzman et al., (eds.), CSH Lab, pp. 68–72 (1988).

Marangos et al., "Neuron Specific Enolase, a Clinically Useful Marker for Neurons and Neuroendocrine Cells," *Ann. Rev. Neurosci.* 10:269–295 (1987).

Margolis et al., "Identifying HSV Infected Neurons After Ocular Inoculation," *Current Eye Res.* 6(1):119–126 (1987).

Margolis et al., "Pathways of Viral Gene Expression During Acute Neuronal Infection with HSV–1," *Virology* 189:150–160 (1992).

Margolis et al., "Selective Spread of Herpes Simplex Virus In the Central Nervous System After Ocular Inoculation," *J.*

Virol. 63(11):4756–4761 (1989).

Martuza et al., "Experimental Therapy of Human Glioma by Means of a Genetically Engineered Virus Mutant," *Science* 252:854–856 (1991).

Mellerick et al., "Physical State of the Latent Herpes Simplex Virus Genome in a Mouse Model System: Evidence Suggesting an Episomal State," *Virology* 158:265–275 (1987).

Miura et al., "Cell-Specific Expression of the Mouse Glial Fibrillary Acidic Protein Gene: Identification of the *Cis–* and *Trans–*Acting Promoter Elements for Astrocyte–Specific Expression," *J. Neorochem.* 55:1180–1188 (1990).

Norgren et al., "Retrograde Transneuronal Transport of Herpes Simplex Virus in the Retina After Injection in the Superior Colliculus, Hypothalamus and Optic Chiasm," *Brain Res.* 479:374–378 (1989).

Oberdick et al., "A Promoter That Drives Transgene Expression in Cerebellar Purkinje and Retinal Bipolar Neurons," *Science* 248:223–226 (1990).

Palmer et al., "Genetically modified skin fibroblasts persist long after transplantation but gradually inactivate introduced genes," *Proc. Natl. Acad. Sci. USA* 88:1330–1334 (1991).

Palmiter et al., "SV40 Enhancer and Large–T Antigen Are Instrumental in Development of Choroid Plexus Tumours in Transgenic Mice," *Nature* 316:457–460 (1985).

Price et al., "Lineage analysis in the vertebrate nervous system by retrovirus–mediated gene transfer," *Proc. Natl. Acad. Sci. USA* 84:156–160 (1987).

Rock et al., "Detection of Latency–Related Viral RNAs in Trigeminal Ganglia of Rabbits Latently Infected with Herpes Simplex Virus Type 1," *J. Virol.* 61(12):3820–3826 (1987).

Rock et al., "Detection of HSV–1 Genome in Central Nervous System of Latently Infected Mice," *Nature* 302:523–525 (1983).

Roizman et al., "Herpesviruses and Their Replication," in *Virology*, B. N. Fields et al., (eds.), Raven Press, New York, pp. 497–526 (1985).

Sacks et al., "Deletion Mutants in the Gene Encoding the Herpes Simplex Virus Type 1 Immediate–Early Protein ICP0 Exhibit Impaired Growth in Cell Culture," *J. Virol.* 61(3):829–839 (1987).

Sanes et al., "Use of a Recombinant Retrovirus to Study Post–Implantation Cell Lineage in Mouse Embryos," *EMBO J.* 5(12):3133–3142 (1986).

Sawtell et al., "Herpes Simplex Virus Type 1 Latency–Associated Transcription Unit Promotes Anatomical Site–Dependent Establishment and Reactivation from Latency," *J. Virol.* 66(4):2157–2169 (1992).

Shepard et al., "Separation of Primary Structural Components Conferring Autoregulation, Transactivation, and DNA–Binding Properties to the Herpes Simplex Virus Transcriptional Regulatory Protein ICP4," *J. Virol.* 63(9):3714–3728 (1989).

Smibert et al., "Differential Regulation of Endogenous and Transduced β–Globin Genes During Infection of Erythroid Cells with a Herpes Simplex Virus Type 1 Recombinant," *J. Virol.* 64(8):3882–3894 (1990).

Smiley, J. R., "Construction In Vitro and Rescue of a Thymidine Kinase–Deficient Deletion Mutant of Herpes Simplex Virus," *Nature* 285:333–335 (1980).

Spaete et al., "The herpes simplex virus amplicon: analyses of cis–acting replication functions," *Proc. Natl. Acad. Sci. USA* 82:694–698 (1985).

Spivack et al., "Detection of Herpes Simplex Virus Type 1 Transcripts During Latent Infection In Mice," *J. Virol.* 61(12):3841–3847 (1987).

Stevens et al., "RNA Complementary to a Herpesvirus α Gene mRNA is Prominent in Latently Infected Neurons," *Science* 235:1056–1059 (1987).

Stevens, J. G., "Human Herpesviruses: A Consideration of the Latent State," *Microbiol. Rev.* 53(3):318–332 (1989).

Stevens, J. G., "Latent Characteristics of Selected Herpesviruses," *Adv. Cancer Res.* 26:227–256 (1978).

Ugolini et al., "Transneuronal Transfer of Herpes Virus from Peripheral Nerves to Cortex and Brainstem," *Science* 234:89–91 (1989).

Wagner et al., "Physical Characterization of the Herpes Simplex Virus Latency–Associated Transcript in Neurons," *J. Virol.* 62(4):1194–1202 (1988).

Wigdahl et al., "Herpes simplex virus latency in isolated human neurons," *Proc. Natl. Acad. Sci. USA* 81:6217–6221 (1984).

DeLuca et al., "Physical and Functional Domains of the Herpes SimplexVirus Transcriptional Regulatory Protein ICP4," *J. Virol.* 62:732–743 (1988).

Sakimura et al., "The structure and expression of neuron-–specific enolase gene," *Gene* 60:103–113 (1987).

Field et al., "The pathogenicity of thymidine kinase–deficient mutants of herpes simplex virus in mice," *J. Hyg. Camb.* 81:267∝277 (1978).

Boothman, David A. et al., "Expression of the *E. coli* Lac Z Gene from a Defective HSV–1 Vector in Various Human Normal, Cancer–Prone and Tumor Cells", *FEBS* 258(1):159–162 (Nov. 1989).

Chiocca, E. Antonio et al., "Transfer and Expression of the *lacZ* Gene in Rat Brain Neurons Mediated by Herpes Simplex Virus Mutants", *New Biol.* 2(8):739–746 (Aug. 1990).

Denniston, K. J. et al., "Characterization of Coliphage Lambda Hybrids Carrying DNA Fragments from *Herpes simplex* Virus Type 1 Defective Interfering Particles", *Gene* 15:364– 378 (1981).

During, M. J. et al., "Neuronal Expression of Parvalbumin and Calcium/Calmodulin Dependent Protein Kinase II from HSV–1 Vectors", *Abstr. Soc. Neurosci.* 16:501 [Abstr. No. 216.4] (Aug. 1990).

Enquist, L. W. et al., "Cloning of Herpes Simplex Type 1 DNA Fragments in a Bacteriophage Lambda Vector", *Science* 203:541–544 (Feb. 9, 1979).

Federoff, H. J. et al., "Neuronal Specific Expression of the Human Neurofilament L Promoter in a HSV–1 Vector", *Abstr. Soc. Neurosci.* 16:353 [Abstr. No. 154.2] (Aug. 1990).

Freese, Andrew et al., "HSV–1 Vector Mediated Neuronal Gene Delivery", *Biochem. Pharm.* 40(10):2189–2199 (1990).

Frenkel, Niza et al., "Defective Virus Vectors (Amplicons) Derived from Herpes Simplex Viruses", *Gene Transfer and Cancer*, pp. 105–113, M. L. Pearson and N. L. Sternberg (eds.), Raven Press, N.Y. (1984).

Frenkel, Niza et al., "The Herpes Simplex Virus Amplicon—A Novel Animal–virus Cloning Vector", *Eukaryotic Viral Vectors*, pp. 205–209, Cold Spring Harbor Laboratory Press, Cold Spring Harbor, N.Y. (1982).

Geller, Alfred I. et al., "An Efficient Deletion Mutant Packaging System for Defective Herpes Simplex Virus Vectors: Potential Applications to Human Gene Therapy and Neuronal Physiology", *PNAS USA* 87:8950–8954 (Nov. 1990).

Geller, Alfred I. et al., "Expression of the Human Tyrosine Hydroxylase Gene in Cultured Fibroblasts and Striatal Neurons from a HSV–1 Vector: Possible Gene Therapy for Parkinson's Disease", *J. Cell Biol.* *III(5)* [Part 2]:339a [Abstr. No. 1899] (1990).

Geller, Alfred I. et al., "Herpes Simplex Virus–1 (HSV–1) Vector System for Introduction of Foreign Genes to Rat Brain Neuron", *Chem. Abstr.* 112(5):128 [Abstr. No. 31241q] (Jan. 29, 1990).

Geller, Alfred I. et al., "Infection of Cultured Central Nervous System Neurons with a Defective Herpes Simplex Virus 1 Vector Results in Stable Expression of *Escherichia coli* β–Galactosidase", *PNAS USA* 87:1149–1153 (Feb. 1990).

Geller, Alfred I., "Influence of the Helper Virus on Expression of β–Galactosidase from a Defective HSV–1 Vector, pHSVlac", *J. of Vir. Meth.* 31:229–238 (1991).

Geller, Alfred I., "A New Method to Propagate Defective HSV–1 Vectors", *Nucl. Acids Res.* 16(12):5690 (1988).

Geller, Alfred I., "A System, Using Neural Cell Lines, to Characterize HSV–1 Vectors Containing Genes which Affect Neuronal Physiology, or Neuronal Promoters", *J. Neurosci. Met.* 36:91–103 (1991).

Geller, Alfred I. et al., "Transfection of Neurons with a Defective HSV–1 Vector and Expression of β–Galactosidase", *Abstr. Soc. Neurosci.* 14(Part I):624 [Abstr. No. 254.11] (Aug. 1988).

Holloway, Marguerite, "Neural Vector—Herpes May Open the Way to Gene Therapy in Neurons", *Sci. Am.* 264:32 (Jan. 1991).

Kwong, Ann D. et al., "Herpes Simplex Virus Amplicon: Effect of Size on Replication of Constructed Defective Genomes Containing Eucaryotic DNA Sequences", *J. Virol.* 51(3):595–603 (Sep. 1984).

Kwong, Ann D. et al., "The Herpes Simplex Virus Amplicon: Efficient Expression of a Chimeric Chicken Ovalbumin Gene Amplified within Defective Virus Genomes", *Virology* 142:421–425 (1985).

Neve, R. L. et al., "Fusion of the Aminoterminal 10 Amino Acids of GAP–43 to Beta–Galactosidase Targets the Chimeric Protein to Neuronal Processes", *Abstr. Soc. Neurosci.* 16:50 [Abstr. No. 27.6] (Aug. 1990).

Palella, Thomas D. et al., "Expression of Human HPRT mRNA in Brains of Mice Infected with a Recombinant Herpes Simplex Virus–1 Vector", *Gene* 80:137–144 (1989).

Paterson, T. et al., "Mutational Dissection of the HSV–1 Immediate–Early Protein Vmw175 Involved in Transcriptional Transactivation and Repression", *Virology* 166:186–196 (1988).

Shih, Meng–Fu et al., "Expression of Hepatitis B Virus S Gene by Herpes Simplex Virus Type 1 Vectors Carrying α– and β–Regulated Gene Chimeras", *PNAS USA* 81:5867–5870 (Sep. 1984).

Smiley, James R. et al., "Expression of a Cellular Gene Cloned in Herpes Simplex Virus: Rabbit Beta–Globin Is Regulated as an Early Viral Gene in Infected Fibroblasts", *J. Virol.* 61(8):2368–2377 (Aug. 1987).

Spaete, Richard R. et al., "The Herpes Simplex Virus Amplicon: A New Eucaryotic Defective–Virus Cloning–Amplifying Vector", *Cell* 30:295–304 (Aug. 1982).

Stevens, J. G., "Latent Herpes Simplex Virus and the Nervous System", *Curr. Topics in Microbiol. and Immunol.* 70:31–50 (1975).

Vlazny, Donald A. et al., "Replication of Herpes Simplex Virus DNA: Localization of Replication Recognition Signals within Defective Virus Genomes", *PNAS USA* 78(2):742–746 (Feb. 1981).

Breakefield et al., "Gene Transfer into the Nervous System," *Mol. Neurobiol.* 1:339–371 (1987).

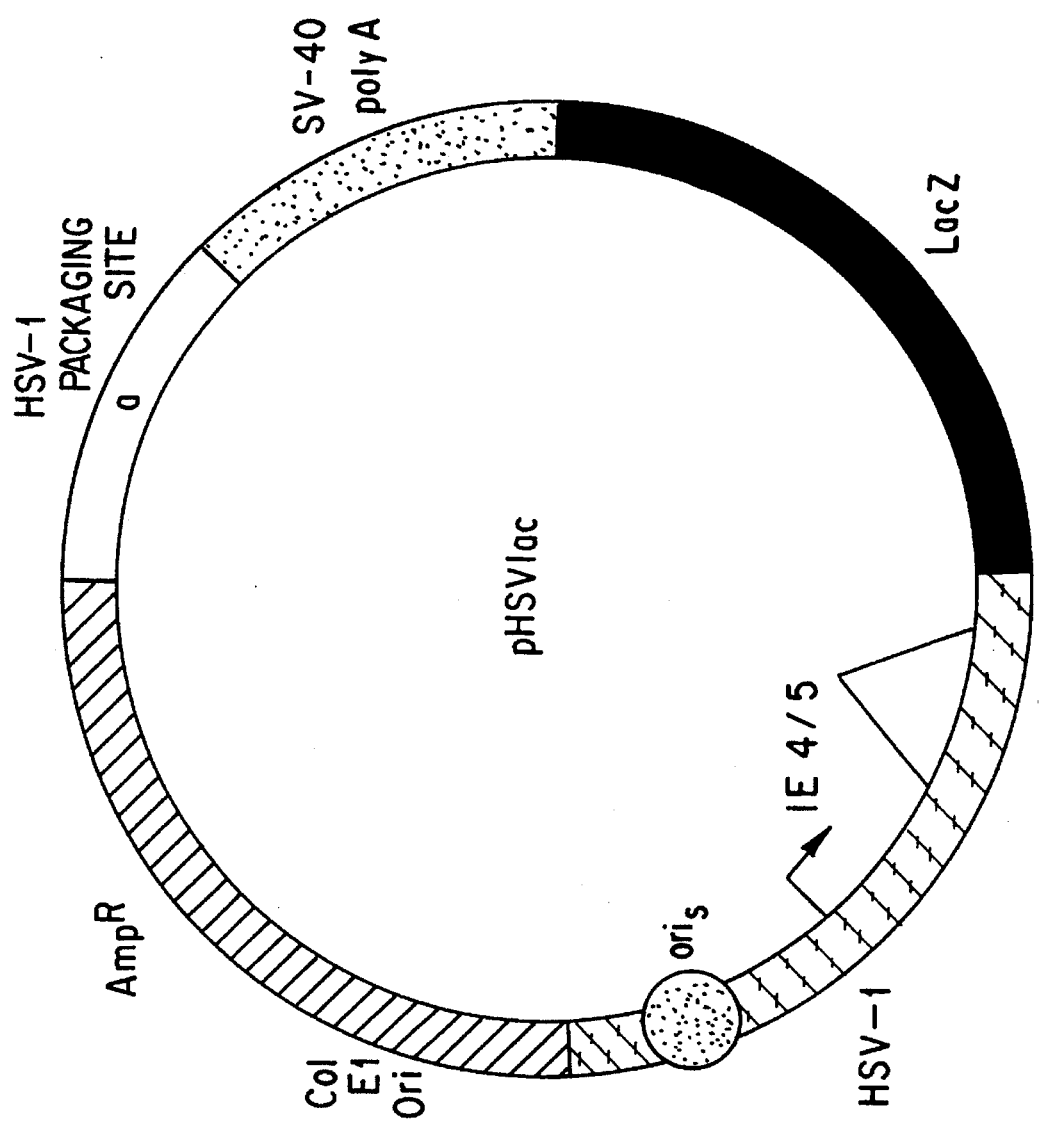

HERPES SIMPLEX VIRUS TYPE I EXPRESSION VECTOR

This application is a continuation of application Ser. No. 07/913,977, filed Jul. 16, 1992, now abandoned, which is a continuation of application Ser. No. 07/304,619, filed Feb. 1, 1989, now abandoned.

FIELD OF THE INVENTION

The present invention relates to a defective herpes simplex type I vector capable of expressing a gene product in eukaryotic cells. The invention further pertains to the use of this vector in introducing and expressing gene sequences in post-mitotic cells such as neurons and in other cells of the nervous system. This invention was made with Federal funds, the Government has certain rights in this invention.

INFORMATION DISCLOSURE STATEMENT

Presented below is a listing of documents known to Applicant and/or his attorney in compliance with the requirements of 37 CFR § 1.56.

The presentation of these documents should not be construed as an admission that any of them are "prior art" under 35 U.S.C. §§102, 103 with respect to this application nor should this statement be construed as a representation that a thorough search has been made or that no more pertinent documents exist. In particular, additional documents of relevance are cited throughout the specification below.

Suhar, T. S. et al. (*Abstr. Amer. Soc. Microbiol.* 1985, p286, Abstr. S27) describe the use of a transient expression system to assay the strength of HSV promoters.

Marchioli, C. C. et al. (*Abstr. Amer. Soc. Microbiol.* 1985, p286, Abstr. S28) describe the use of a recombinant HSV-1 vector, capable of expressing a major excreted glycoprotein of pseudorabies, to infect VERO cells in an effort to induce immunity to pseudorabies virus in mice.

Yan, D. -H. et al. (*Abstr. Amer. Soc. Microbiol.* 1985, p286, Abstr. S30) describe a recombinant vector containing the HSV-1 thymidine kinase gene.

Geller, A. I. (*Nucl. Acid Res.* 16:5690 (1988)) discloses a method for propagating HSV-1 vectors.

Geller, A. I. et al. (*Science* 241:1667–1669 (1988)) describes the pHSVlac vector of the present invention.

Breakefield, X. O. et al. (*Molec. Neurobiol.* 1:339–371 (1987)), describes methods and vectors for treating neuronal diseases. This reference discusses HSV-1 vectors on page 360. The reference is believed to have been first made available to the public on Feb. 1, 1988.

Sugden, W. M. (U.S. Pat. No. 4,686,186) discloses recombinant vectors which are composed of a lymphotrophic Herpes virus such as Epstein-Barr virus. HSV-1 is not a lymphotrophic virus.

Bear, S. E. et al. (*J. Molec. Appd. Genet.* 2:471–484 (1984)) describe HSV-1 shuttle vectors.

Shih, M. -F. et al. (In: *Vaccines* 85, Cold Spring Harbor Press, Cold Spring Harbor, N.Y. (1985) pp 177–180) provide a discussion concerning the potential uses of HSV-1 as a vector for eukaryotic viral genes.

Palella, T. D. et al. (*Molec. Cell. Biol.* 8:457–460 (1988)) suggests the use of HSV-1 as a vector for transferring the HGPRT gene into neuronal cells.

Robbins, A. K. et al. (*J. Molec. App. Genet.* 2:485–496 (1984)) describe a vector which contained sequences of the Pseudorabies virus and the *E. coli* β-galactosidase gene.

Matz, B. et al. (*J. Gen. Virol.* 64:2261–2270 (1983)) is cited to illustrate the HSV-1 strain 17 ts K. Additional references discussing this strain are provided below.

BACKGROUND OF THE INVENTION

The capacities to introduce a particular foreign or native gene sequence into a mammalian cell and to control the expression of that gene are of substantial value in the fields of medical and biological research. Such capacities provide a means for studying gene regulation, for defining the molecular basis of a disease, and for designing a therapeutic basis for the treatment of disease.

Gene transfer techniques can be used for two general purposes. First, they can be used to evaluate the regulation and function of a cloned gene following its modification and introduction into different cell types by studying, for example, the definition of the regulatory elements that control levels of gene expression, alternate modes of RNA splicing, post-translational processing of peptides, sorting of proteins to their appropriate cellular locations, and biological activities of proteins. Second, gene transfer techniques can be used to modify cells, such as those of the nervous system, in culture and in vivo. Such studies may, for example, involve analysis of cell lineage, alternation of phenotypic properties, and ablation of specific cell populations, as well as creation and correction of hereditary disease states. Gene transfer techniques can thus be used as a tool in understanding molecular aspects of the development, function, and survival of cells.

The introduction of a particular foreign or native gene into a mammalian host cell is facilitated by first introducing the gene sequence into a suitable nucleic acid vector. A variety of methods have been developed which are capable of permitting the introduction of such a recombinant vector into a desired host cell.

For example, such a recombinant vector can be introduced into the host cell by DNA-mediated transformation (Choo, K. H. et al., *Gene* 46:277–286 (1986); Perez, C. F. et al., *Radiat. Res.* 104:200–213 (1985); Horst, J. et al., *Hoppey-Seyler's Z. Physiol. Chem.* 363:445– 448 (1982); Hirschhorn, R. R. et al., *Fed. Proc.* 41: Abstract 6525 (1982); Graham, F. L. et al., In: *The Wistar Symposium Series, Volume 1 Introduction of Macromolecules into Viable Mammalian Cells*, Alan R. Liss, Inc., New York, N.Y. page 3–26 (1980); Upcroft, P., *Anal. Biochem.* 162:1–4 (1987)). The vector can also be introduced into a mammalian cell by protoplast fusion (Yoakum, G. H., *Biotechniques* 2:24– 26, 28–30 (1984)), or by micro-injection (Spandidos, D. A. et al., *Eur. J. Cell. Biol.* 37:234–239 (1985); Folger, K. R. et al., *Molec. Cell. Biol.* 2:1372–1387 (1982); Gordon, J. W. et al., *Proc. Natl Acad. Sci. USA* 77:7380–7384 (1980)). Unfortunately, the above-described techniques are relatively inefficient and unsuitable for use in situations which require that the recombinant molecule be introduced into all or most of the cells present in culture or in an animal.

Techniques of transgenic genetics have been used to achieve the efficient introduction of a cloned gene sequence into all or most of the cells of an animal. In such an approach, a recombinant plasmid is introduced into the pronuclei of a fertilized egg and permitted to develop into a transgenic animal. Such an animal will usually contain the introduced gene in all of the cells of its body including its germ line. Transgenic genetics is, however, a technically difficult and exacting procedure.

Viral vectors have been employed in order to increase the efficiency of introducing a recombinant vector into suitably sensitive host cells. Viruses which have been employed as vectors for the transduction and expression of exogenous genes in mammalian cells include SV40 virus (Chung, M. H. et al., *Korean J. Microbiol.* 25:165– 172 (1987); Innis, J. W. et al., *Molec. Cell. Biol.* 3:2203–2210 (1983); Okayama, H. et al., *Molec. Cell. Biol.* 5:1136–1142 (1985)), bovine papilloma virus (Meneguzzi, G. et al., *Embo. J.* 3:365–372 (1984); Dimaio, D. et al., *Proc. Natl. Acad. Sci. USA* 79:4030–4034 (1982); Lusky, M. et al., *Cell* 36:391–402 (1984); Giri, I. et al. *Virol.* 127:385–396 (1983); Lusky, M. et al., *Molec. Cell. Biol.* 3:1108–1122 (1983)), etc.

Retroviruses which have been employed as vectors for the transduction and expression of exogenous genes in mammalian cells include the Moloney murine sarcoma virus (Perkins, A. S. et al., *Molec. Cell. Biol.* 3:1123–1132 (1983); Lee, W. H. et al., *J. Virol.* 44:401–412 (1982); Curran, T. et al., *J. Virol.* 44:674–682 (1982); Gazit, A. et al., *J. Virol.* 60:19–28 (1986)), etc. In contrast to methods which involve DNA transformation or transfection, the use of viral vectors can result in the rapid introduction of the recombinant molecule into a wide variety of host cells.

Efforts to introduce recombinant molecules into post-mitotic neurons and other neural cells have, however, been hampered by the inability of such cells to be infected by the above-described viral or retroviral vectors. Thus, the study of gene expression in neuronal cells, and the identification of therapies for treating neuronal disease have been hampered by the lack of suitable methods to accomplish gene transfer into neural cells. A need therefore exists for efficient viral vectors capable of mediating gene transfer into such cells.

SUMMARY OF THE INVENTION

The invention concerns a recombinant HSV-1 vector capable of infecting and persisting in a non-mitotic cell. The vector can be used to treat neurological diseases, and to produce animal and in vitro models of such diseases. In detail, the invention provides a recombinant HSV-1 vector capable of infecting a neuronal cell, wherein the vector contains:

(1) an HSV-1 packaging site-containing sequence;

(2) an HSV-1 origin of DNA replication-containing sequence; and (3) a heterologous reporter or selectable marker gene sequence sufficient to permit the recognition or selection of the vector.

The invention also concerns the above recombinant vector which additionally contains one or more of the following sequences:

(4) a promoter sequence sufficient to direct transcription of a distally located sequence in a neuronal cell;

(5) a sequence sufficient to direct translation of a distally located sequence in a neuronal cell;

(6) a sequence sufficient to permit a neuronal cell to process an expressed protein;

(7) a sequence sufficient to permit the propagation of the vector in a bacteria; or (8) an inserted gene sequence wherein the inserted gene sequence is inserted into the vector such that it is operably linked to the sequences (4), (5) and (6).

The invention further concerns the above-described recombinant vectors which are capable of persisting in a non-mitotic cell.

The invention further concerns the above-described recombinant vector which is pHSVlac.

The invention further concerns the above-described recombinant vector wherein the inserted gene sequence (8) is a gene sequence associated with a disease selected from the group consisting of: lysosomal storage disease, the Lesch-Nyhan syndrome, amyloid polyneuropathy, Alzheimer amyloid, and Duchenne's muscular dystrophy.

The invention further concerns a method for expressing a gene sequence in a non-mitotic cell which comprises:

(a) operably linking the gene sequence to a promoter sequence of a recombinant vector capable of persisting in the non-mitotic cell;

(b) introducing the vector into the cell; and (c) permitting the vector to express the gene in the cell.

The invention further concerns a method for treating a neurological deficiency state disease which comprises:

(a) operably linking a gene sequence whose gene product complements the deficiency of the deficiency state disease to a promoter sequence of a recombinant vector capable of propagation in a neuronal cell;

(b) introducing the vector into the cell; and (c) permitting the vector to express the gene in the cell, wherein the expression complements the deficiency.

The invention further concerns a method for identifying an agent capable of treating a neurological unbalanced state disease which comprises:

(a) operably linking a gene sequence whose expression is sufficient to induce the unbalanced state disease in an animal to a promoter sequence of a recombinant vector capable of propagation in a neuronal cell;

(b) introducing the vector into the cell; and (c) permitting the vector to express the gene in the cell, wherein the expression induces the unbalanced state disease;

(d) providing to the cell an agent suspected of being able to treat the unbalanced state disease in the cell; and (e) identifying any agent capable of treating the unbalanced state disease in the cell.

BRIEF DESCRIPTION OF THE FIGURE

FIG. 1 shows the structure of pHSVlac. The clear region contains the HSV-1 a segment nucleotides 127 to 1132, the packaging site (Davison, A. J. et al., *J. Gen. Virol.* 55:315 (1981)). The cross hatched region symbolizes the HSV-1 c region, nucleotides 47 to 1066 (McGeoch, D. J. et al., *Nucleic Acids Res.* 14:1727 (1986)). pHSVlac was constructed from pCH110 (Hall, C. V. et al., *J. Molec. App. Genet.* 2:101 (1983)).

DESCRIPTION OF THE PREFERRED EMBODIMENTS

I. Methods for Introducing Gene Sequences into Neuronal and Other Post-Mitotic Cells The present invention concerns a means for introducing gene sequences into cells of the nervous system such as neurons, neuroglial cells, etc. Such cells are collectively described herein as "neural or neuronal" cells. Neural cells are described, for example, by Barr, M. L., *The Human*

*Nervous System An Anatomic Viewpoint,* 3rd. Ed., Harper & Row, NY (1979), which reference is herein incorporated by reference).

To study the functions of cloned neuronal genes, methods are required to deliver genes into the cells of the nervous system. Of the four approaches used to introduce genes into cells (the frog oocyte micro-injection system (Noda, M. et al., *Nature* 302:818 (1983)), transgenic mice (Palmiter, R. D. et al., *Science* 222:809 (1983)), transfection of DNA directly into cells (Graham, F. L. et al., *Virology* 52:456 (1973)), and retrovirus vectors (Mann R. et al., *Cell* 33:153 (1983)) none can deliver a gene directly into non-mitotic cells.

Although delivery of recombinant molecules into the cells of the nervous system prior to birth can be accomplished using transformation or micro-injection, delivery into such cells after birth presents complications because of the relative inaccessibility of the cells, their diversity, and the post mitotic state of mature neurons. Thus, such methods are relatively unsuitable for introducing gene sequences into neuronal cells.

In view of the above-stated deficiencies of existing techniques for introducing gene sequences into a neural cell, it would be highly desirable to develop suitable viral vectors which could be employed to deliver such sequences to neural cells. The development of such a gene sequence delivery system is one aspect of the present invention. Methods for introducing gene sequences into neuronal cells are reviewed by Breakefield, X. O. et al., *Molec. Neurobiol.* 1:339–371 (1987), which reference is herein incorporated by reference in its entirety).

A viral vector, as that term is used herein, is a nucleic acid molecule (preferably of DNA) in which a gene sequence (which is to be transferred) is fused to a subset of viral sequences. The viral sequences and the total genome size is selected such that the vector is capable of being encapsulated in a virus particle and thus is capable of binding to, and introducing its gene sequences into a virus-sensitive host cell. The infective properties of such a virion are, thus, the same as those containing the wild type viral genome.

The term "gene sequence," as used herein, is intended to refer to a nucleic acid molecule (preferably DNA). Such gene sequences may be derived from a variety of sources including DNA, cDNA, synthetic DNA, RNA, or combinations thereof. Such gene sequences may comprise genomic DNA which may or may not include naturally occurring introns. Moreover, such genomic DNA may be obtained in association with promoter regions or poly A sequences. The gene sequences of the present invention are preferably cDNA. Genomic DNA or cDNA may be obtained in any of several ways. Genomic DNA can be extracted and purified from suitable cells by means well-known in the art. Alternatively, mRNA can be isolated from a cell and used to produce cDNA by reverse transcription, or other means.

In order to produce the viral vectors of the present invention, several factors are preferably considered. First, since the vector will be delivered only into those cells that can be infected (either abortively or productively) by the wild type virus, it is necessary to produce the viral vector from a wild type virus which is capable of infecting neuronal cells. One must also consider the ability of the viral vector to infect cells in tissue culture or in vivo.

Second, since it may be desirable to maintain the vector and to express the cloned gene sequence for an extended period of time, the virus employed should be capable of persisting in a cell for an extended period of time without causing cell death.

Third, since viral vectors can be produced from viruses which are maintained in either the nucleus or the cytoplasm of a neuronal cell, one must consider whether one desires the viral gene fusion to be maintained in the nucleus or in a cytoplasm of the recipient cell. If, for example, the viral vector exists as a double stranded DNA molecule in the nucleus of a cell, than its transcription may retain appropriate responses to cellular trans-acting regulatory factors. In contrast, if a viral vector is maintained in the cytoplasm, it may not encounter such trans-acting regulatory factors, and therefore, not be subjected to regulation.

Fourth, since the size of the virus genome determines an upper limit on the size of the vector and the gene sequences that can be inserted in it, it is necessary to produce the viral vector from a virus whose size is sufficiently large that it may be adapted to contain an inserted gene sequence of desired size.

In selecting a viral vector system capable of delivering gene sequences to neuronal cells, it has been found to be most desirable to employ a DNA virus whose site of replication is in the nucleus of infected cells. It has further been found desirable for the virus to be capable of latent infection (i.e., persisting in an infected cell without causing cell death). Preferably, the viral vector should also be of substantial size in order that viral derivatives can be formed which are capable of containing substantial amounts of introduced gene sequences. The attributes of such a virus have been found to be present in Herpes Simplex Virus-1 ("HSV-1") (Breakefield, X. O. et al., *Mol. Neurobiol.* 1:339 (1987); Geller, A. I. et al. Science:241:1667–1669 (1988), which reference is herein incorporated by reference in its entirety).

Herpes Simplex Virus-1

HSV-1 is a double-stranded DNA virus which is replicated and transcribed in the nucleus of the cell. In virions, HSV-1 vectors are composed of head to tail repeats (Stow, N. D. et al., *Eukaryotic Viral Vectors,* Y. Gluzman, Ed. (Cold Spring Harbor Laboratory, Cold Spring Harbor, N.Y., 1982), pp. 199–204; Spaete, R. R. et al., *Cell* 30:285 (1982)). The genes of HSV-1 are transcribed by the cellular RNA polymerase II. HSV-1 contains approximately 100 genes and is approximately 150 kilobases in size. Five immediate early ("IE") genes encode the major regulatory proteins of the virus. Immediate early genes induce expression of the early ("E") genes that are responsible for DNA replication. The late ("L") genes are induced after DNA replication and encode the structural components and enzymes required for assembly of virus particles. When the late genes are induced, transcription of the immediate early genes is reduced.

HSV-1 possesses both a lytic and a latent cycle. During the lytic cycle of HSV-1, expression of the three classes of genes occurs in a complex sequential cascade. In contrast, in its latent cycle, HSV-1 gene expression is limited to at most the IE genes and a latency associated transcript (Wagner, E. K. et al., *Science* 235:1056 (1987); Deatly, A. M. et al., *Proc. Natl. Acad. Sci. USA* 84:3204 (1987); Wagner, E. K. et al., *J. Virol.* 62:1194 (1988); Green, M. T. et al., *Infect. Immunol.* 34:987 (1981); Persson, R. H. et al., *J. Virol.* 54:414 (1985); Mosca, J. D. et al., *J. Virol.* 56:867 (1985)). DNA replication does not occur and no progeny virus are produced (Stevens, J. G., *Current Topics in Microbiology and Immunology* 70:31 (1975)).

Thus, in both lyric and latent states, extensive gene regulation occurs which closely mimics the regulation of cellular genes. Electrophysiological properties are unaltered in latently infected neurons (Fukuda, J. et al., *Brain Res.* 262:79 (1983)).

HSV-1 has a wide host range, and infects many cell types in mammals and birds (including chickens, rats, mice, monkeys, and humans) (Spear, P. G. et al., *DNA Tumor Viruses*, J. Tooze, Ed. (Cold Spring Harbor Laboratory, Cold Spring Harbor, N.Y., 1981), pp. 615– 746). HSV-1 can lytically infect a wide variety of cells including neurons, fibroblasts, and macrophages. In addition, HSV-1 infects post-mitotic neurons in adult animals and can be maintained indefinitely in a latent state (Stevens, J. G., *Current Topics in Microbiology and Immunology* 70:31 (1975)).

Post-mitotic neurons harbor HSV-1 in the virus' latent state (Stevens, J. G., *Curr. Top. Microbiol. Immunol.* 70:31–50 (1975)). Once HSV-1 attains latency, it can be retained for the life of the neuron. As mentioned above, latent HSV-1 is capable of expressing genes; expression of genes encoded by HSV-1 has been detected by immunochemistry in latently infected neurons. Furthermore, HSV-1 is transported both anterogradely and retrogradely in neurons. This property is especially advantageous in that it suggests that HSV-1 vectors will be capable of reaching cells of interest some distance away from the injection site.

Among the immortal neuronal cell lines that can be infected by HSV-1 include the mouse neuroblastoma cell lines NS20Y and N1E-115, and the rat pheochromocytoma cell line PC12. HSV-1 virions can be detected in neurons in vivo by electron microscopy (Cook, M. L. et al., *Infect. Immunity.* 9:946–951 (1974)). Two lines of evidence suggest that HSV-1 can infect most, if not all, kinds of neurons in the central nervous system. First, following inoculation of HSV-1 in the periphery, a burst of virus production ascends the neuroaxis, initially in the sensory or motor neurons innervating the site of inoculation, then in the spinal cord, brain stem, cerebellum, and cerebral cortex (Koprowski, H., In: *Persistent Viruses* (Stevens, F. G., ed.), pp. 691–699, Academic Press, NY (1978)). Second, attempts to mimic HSV-1 latency in tissue culture with different preparations of neurons have required high temperature, DNA synthesis inhibitors, and antisera directed against HSV-1 virions to prevent a lytic infection for spreading to all the neurons (Wigdahl, B., et al., *Proc. Natl. Acad. Sci. USA* 81:6217–6201 (1984)).

The HSV-1 Vectors of the Present Invention

The preferred vectors of the present invention are produced from HSV-1. The HSV-1 vectors of the present invention will preferably contain:

(1) a sequence which contains an HSV-1 packaging site (preferably the HSV-1 a segment located at approximately nucleotides 127–1132 of the a sequence of HSV-1 virus, or its equivalent) (Davison, A. J. et al., *J. Gen. Virol.* 55:315 (1981) such that the vector can be packaged into a particle which is capable of adsorbing to a cell;

(2) a sequence which contains an HSV-1 origin of DNA replication (preferably the HSV-1 c region, containing the HSV-1 $ori_s$ region, located at approximately nucleotides 47–1066 of HSV-1 virus, or its equivalent) (McGeoch, D. J. et al., *Nucleic Acids Res.* 14:1727 (1986)); and (3) a reporter or selectable marker gene sequence sufficient to permit the recognition or selection of the vector in a host cell. A reporter gene sequence, as used herein, is any gene sequence which, when expressed, results in the production of a protein whose presence or activity can be easily monitored. As used herein, a reporter or selectable marker gene sequence is said to be "heterologous" if it is not naturally present in a wild type HSV-1 genome. Examples of suitable reporter genes include the gene for galactokinase, beta-galactosidase, chloramphenicol acetyltransferase, beta-lactamase, etc.

Alternatively, the reporter gene sequence may be any gene sequence whose expression produces a gene product which affects neuronal physiology (including components of second messenger systems or neurotransmitter metabolism, or ion channels.

A selectable marker gene sequence is any gene sequence capable of expressing a protein whose presence permits one to selectively propagate a cell which contains it. Examples of selectable marker gene sequences include gene sequences capable of conferring host resistance to antibiotics (such as ampicillin, tetracycline, kanamycin, streptokinase, etc.), of conferring resistance to amino acid analogues, of permitting the growth of the bacteria on additional carbon sources or under otherwise impermissive culturing conditions. A gene sequence may be both a reporter gene sequence and a selectable marker gene sequence; The most preferred reporter gene of the present invention is the lacZ gene which encodes the beta-galactosidase activity of *E. coli*. The most preferred selectable marker sequence is the beta-lactamase gene of pBR322;

The most preferred reporter or selectable marker gene sequence sufficient to permit the recognition or selection of the vector in a neuronal cell. Preferably, the selected reporter gene sequence will encode an enzyme or other protein which is normally absent from mammalian cells, and whose presence can, therefore, definitively establish the presence of the vector in such a cell. The most preferred such sequence being the *E. coli* lacZ gene (Sanes, J. R. et al., *EMBO J.* 5:3133 (1986); Price, J. et al., *Proc. Natl. Acad. Sci. USA* 84:156 (1987)).

An even more preferred vector of the present invention will, in addition to the above-enumerated sequences (1), (2) and (3), contain one or more of the following sequences:

(4) a sequence, such as a promoter sequence, sufficient to direct the transcription of a distally located sequence (i.e. a sequence linked to the 5' end of the promoter sequence) in a neuronal cell. The most preferred such sequence being the HSV-1 IE 4/5 promoter sequence (McGeoch, D. J. et al., *Nucleic Acids Res.* 14:1727 (1986)).

(5) a sequence, such as an ATG or other initiation codon, sufficient to direct the translation of the distally located sequence in a neuronal cell. The most preferred such sequence being the sequence which follows the HSV-1 IE 4/5 promoter sequence;

(6) a sequence, such as a polyadenylation sequence, a localization sequence, a signal sequence, or a termination sequence, sufficient to permit a neuronal cell to efficiently and effectively process the expressed protein. The most preferred polyadenylation sequence being the SV40 early region polyadenylation site (Hall, C. V. et al., *J. Molec. App. Genet.* 2:101 (1983));

(7) a sequence sufficient to permit the propagation of the viral vector in a bacteria, such as *E. coli*. Such a sequence may comprise only an origin of replication, or may comprise an entire plasmid capable of replicating in the bacteria. For example, in a preferred embodiment, the bacteria is *E. coli,* and the sequence can be either an *E. coli* ori sequence or (even more preferably) a plasmid such as Col E1, pBR322, etc. The most preferred such sequence contains the Col E1 origin of replication of pBR322. The entire pBR322 plasmid may be employed;

An even more preferred vector of the present invention will, in addition to one or more of the above-enumerated sequences, contain:

(8) one or more inserted sequences whose introduction, transcription, or expression in a neuronal cell is desired. Such sequences are inserted into the vector in order to operably link the sequence with the promoter sequence (4), if transcription is desired, or additionally with the initiation and processing sequences (5 and 6), if translation and processing are desired. Alternatively, the inserted sequence may be placed at any position in the vector. The term "operable linkage" is intended to describe a linkage between a gene sequence and a promoter or other regulatory or processing sequence such that the transcription of the gene sequence is directed by an operably linked promoter sequence, the translation of the gene sequence is directed by an operably linked translational regulatory sequence, and the post-translational processing of the gene sequence is directed by an operably linked processing sequence.

It is, of course possible to employ, as the inserted gene sequence a gene sequence which already possesses a promoter, initiation sequence, or processing sequence. In such a case, it would be unnecessary to employ a viral vector which additionally contained these sequences.

As will be appreciated by one of ordinary skill, the nucleotide sequence(s) of the inserted gene sequence or sequences may be of any nucleotide sequence.

The viral vectors of the present invention are preferably from 5 to 15 kb in size, and encapsulated in the HSV-1 viral particle as head to tail repeats of varying length up to 150 kb (the size of wild type HSV-1). HSV-1 contains three origins of DNA replication (ori), or one ori every 50 kb, while the above-described vector contains one origin of DNA replication every 5 kb to 15 kb (Stow, N. D. et al., *Eukaryotic Viral Vectors*, Y. Gluzman, Ed. (Cold Spring Harbor Laboratory, Cold Spring Harbor, N.Y., 1982), pp. 199–204; Spaete, R. R. et al., *Cell* 30:285 (1982)).

Viral stock containing any of the viral vectors of the present invention can be preferably obtained by transfecting fibroblasts with a mixture of vector DNA and helper HSV-1 DNA (Stow, N. D. et al., *Eukaryotic Viral Vectors*, Y. Gluzman, Ed. (Cold Spring Harbor Laboratory, Cold Spring Harbor, N.Y., 1982), pp. 199–204; Spaete, R. R. et al., *Cell* 30:285 (1982)). In such an infection, the vectors are maintained and propagated because their possession of an increased number of origins of replication provide them with a growth advantage over the helper virus (Frenkel, N., et al., *Ann. N.Y. Acad. Sci.* 354:347–370 (1980)). Alternatively, the vector can be propagated according to the manner of Geller, A. I. (*Nucl. Acid Res.* 16:5690 (1988)).

Although it is possible to propagate the HSV-1 viral vector using a wild type HSV-1 virus (as a helper virus), infection of neuronal cells with wt HSV-1 invariably causes some cell death. Since such cell death is especially undesirable for many gene expression studies, it is especially preferred to propagate the HSV-1 vector using an HSV-1 helper virus which has a mutation, most preferably a temperature sensitive mutation, which prevents the helper virus from entering the lyric cycle (thereby preventing cell damage) when the neuronal cell infection is carried out at a viral growth restrictive temperature of 37° or 39° C. Such a helper virus can be grown at the viral growth permissive temperature of 31° C.

Intracerebral injection (Watson, K. et al., *J. Gen. Virol.* 49:149 (1980)) and infection of mouse neuroblastoma cells (Gerdes, J. G. et al., *Virology* 94:430 (1979)) with HSV-1 temperature sensitive (ts) mutants allows persistence of the virus without cell death.

Structural and genetic characteristics of the HSV-1 vectors of the present invention can be most clearly illustrated by a description of the most preferred HSV-1 vector: pHSVlac. This defective HSV-1 viral vector contains 8.1 kb of double stranded DNA. The vector is depicted in FIG. 1. pHSVlac contains the following gene sequences:

(1) an HSV-1 packaging site comprising approximately nucleotides 127–1132 of HSV-1 a region;
(2) an HSV-1 origin of DNA replication comprising the HSV-1 c region located at approximately nucleotides 47–1066;
(3) the beta-lactamase gene sequence of pBR322; and
(4) the HSV-1 IE 4/5 promoter sequence;
(5) the intervening sequence (intron) following the HSV-1 IE 4/5 promoter sequence;
(6) the SV40 early region polyadenylation sequence;
(7) the Col E1 origin of replication region of pBR322; and
(8) the *E. coli* lacZ gene (as an inserted gene sequence whose expression in a neuronal cell is readily detectable).

pHSVlac was deposited with the American Type Culture Collection on Jan. 31, 1989, and given the accession number ATCC 40544.

pHSVlac DNA is preferably packaged into HSV-1 virus particles using HSV-1 strain 17 ts K (Davison, M. J. et al., *J. Gen. Virol.*, 65:859 (1984); Brown, S. M. et al., *Proc. Natl. Acad. Sci.* (U.S.A.) 76:2364–2368 (1979); Watson, K., *J. Gen. Virol.* 49:149–160 (1980); Dargan, D. et al., *J. Gen. Virol.* 64:1311–1326 (1983); Matz, B. et al., *J. Gen. Virol.* 64:2261–2270 (1983); Dargan, D. et al., *J. Gen. Virol.* 65:477–492 (1984) as helper virus (herinafter referred to as "ts K"). HSV-1 strain 17 ts K has a mutation in the IE 3 gene. The virus has an immediate early phenotype, and is not permissive for DNA replication at 37°–39° C. It can, however, replicate when cultured at 31° C.

pHSVlac contains three Eco RI sites, one at each end of the pBR322 segment and a third in the lacZ gene 133 bp from the 3' end of the gene. Most of the transcription unit of pHSVlac is present in a 4.3 kb fragment. The pBR322 sequences of pHSVlac are present in a 2.3 kb fragment. The 3' end of the lacZ gene, the SV-40 early region polyadenylation site, and the HSV-1 a sequence are contained in a 1.5 kb fragment of pHSVlac.

Application of Gene Transfer Technology to Neuorscience and Neurochemistry

Gene transfer technology has several applications to neuroscience and neurochemistry. The most immediate applications are, perhaps, in elucidating the process of neural peptides and the functional domains of proteins. Cloned cDNA or genomic sequences for neural proteins can be introduced into different cell types in culture, or in vivo, in order to study cell type-specific differences in processing and cellular fate. By placing the coding sequences under the control of a strong promoter, a substantial amount of the protein can be made, thus avoiding difficulties in characterizing trace amounts. Furthermore, the specific residues involved in protein processing, intracellular sorting, or biological activity can be determined by mutational change in discrete residues of the coding sequence.

Gene transfer technology can also be applied to provide a method to control expression of a protein and to assess its capacity to modulate cellular events. Some functions of neural proteins, such as their role in differentiation, may be studied in tissue culture, whereas others will require reintroduction into the nervous system at different times in development or aging in order to monitor changes in receptor density, cell number, fiber growth, electrical activity, and other relevant properties.

Gene transfer provides a means to study the DNA sequences and cellular factors which regulate expression of neural specific genes. One approach to such a study would be to fuse the regulatory elements to be studied to a particular reporter gene and subsequently assaying for the expression of the reporter gene.

The regulation of gene expression in neuronal cells has been found to have a role in maintaining homeostasis and is believed to have a role in mediating information retention in response to external and internal signals (Black, I. B., et al., *Science* 236:1263–1268 (1987)). During development, coordinate regulation of gene expression serves to produce a differentiated phenotype, e.g., as in catecholamine metabolism and myelin biosynthesis. Regulation depends on many factors including chromatin structure, DNA methylation, and trans-acting factors, which respond to phosphorylation, hormones, and other signals. It is a complex process that allows sets of genes to be expressed together or differentially and may involve a combinatorial code of regulatory sequences.

Issues of cellular fate and interactions in the nervous system can also be addressed by gene transfer. For example, genes which encode histological markers can be introduced into embryonic cells to determine lineage relationships during development and to elucidate neuronal pathways. In addition, genes encoding growth factors, oncogenic proteins, toxic peptides, or other physiologically important proteins, can be introduced into specific areas of the nervous system to study their effects on cell division, survival, and differentiation. For some studies, gene transfer or gene expression must be restricted to specific cells in the nervous system.

Gene transfer also possesses substantial potential use in understanding and providing therapy for disease states. There are a number of inherited neurologic diseases in which defective genes are known and have been cloned. In some cases, the function of these cloned genes is known. In humans, genes for defective enzymes have been identified for (1) lysosomal storage diseases such as those involving β-hexosaminidase (Kornerluk, R. G., et al., *J. Biol. Chem.* 261:8407–8413 (1986); Myerowitz, R., et al., *Proc. Natl. Acad. Sci. USA* 82:7830–7834 (1985)) and glucocerebrosidase (Sorge et al., *Proc. Natl. Acad. Sci. USA* 82:5442–5445 (1985); Tsuji, S., et al., *N. Engl. J. Med.* 316:570–575 (1987)), (2) for deficiencies in hypoxanthine phosphoribosyl transferase activity (the "Lesch-Nyhan" syndrome; Stout et al., *Met. Enzymol.* 151:519–530 (1987)), (3) for amyloid polyneuropathies (prealbumin; Sasaki, H., et al., *Biochem. Biophys. Res. Commun.* 125:636–642 (1984), (4) for Alzheimer amyloid (Tanzi, R. E., et al., *Science* 235:880–884 (1987); Goldgaber, D., et al., *Science* 235:877–880 (1986)); (5) for Duchenne's muscular dystrophy (uncharacterized muscle protein; Monaco, A. P., et al., *Nature* 323:646–650 (1987)); and (6) for retinoblastoma (uncharacterized protein expressed in the retina and other tissues, Lee, W. -H., et al., *Science* 235:1394–1399 (1987); Friend, S. H., et al., *Nature* 323:643–646 (1986)).

Gene transfer techniques can also be used to study the "shiverer" mutation (myelin basic protein, Roach, A., et al., *Cell* 42:149–155 (1987); Molineaux, S. M., et al., *Proc. Natl. Acad. Sci. USA* 83:7542–7546 (1986)) and the "jimpy" mutation (proteolipoprotein, Nave, K. -A., et al., *Proc. Natl. Acad. Sci. USA* 83:9264–9268 (1986); Hudson, L. D., et al., *Proc. Natl. Acad. Sci. USA* 84:1454–1458 (1987)).

The above diseases fall into two classes: deficiency states, usually of enzymes, which are inherited in a recessive manner; and unbalanced states, at least sometimes involving structural or regulatory proteins, which are inherited in a dominant manner.

For deficiency state diseases, gene transfer could be used to bring a normal gene into affected tissues for replacement therapy, as well as to create animal models for the disease using antisense mutations. For unbalanced state diseases, gene transfer could be used to create the disease state in a model system, which could be used in efforts to counteract the effect of the imbalance. Thus, the methods of the present invention permit the treatment of neurological diseases. As used herein, a deficiency state disease is "treated" by partially or wholly remedying the deficiency which causes the deficiency or which makes it more severe. As used herein, an unbalanced state disease is "treated" by partially or wholly remedying the imbalance which causes the disease or which makes it more severe. The use of site-specific integration of DNA sequences to cause mutations or to correct defects is also possible.

In summary, HSV-1 viral vectors, such as pHSVlac, can be used to stably transfect post-mitotic cells such as neurons and stably express β-galactosidase. The *E. coli* lacZ gene is pHSVlac can be exchanged for other coding sequences. Using this vector, it is now possible to introduce, into neurons, genes which encode products that effect physiology, including components of second messenger systems and neurotransmitter metabolism. The vectors of the present invention may be useful for gene therapy on neuronal diseases or for experimental modification of neuronal physiology.

Having now generally described this invention, the same will be better understood by reference to certain specific examples which are included herein for purposes of illustration only and are not intended to be limiting of the invention, unless specified.

EXAMPLE 1

Methods for Cell and Viral Propagation

CV1 monkey fibroblasts were grown in Dulbecco's modified minimum essential medium with 10% fetal calf serum. HSV-1 strain 17 ts K was described by Davison, M. J. et al., *J. Gen. Virol.*, 65:859 (1984)). Cultures of embryonic mouse spinal cord were obtained according to the procedure of Huettner, J. E. et al. (*J. Neurosci.* 6:3044–3066 (1986)). Cultures of striatum and total neocortex (Freese A. et al., *Proc. Soc. Neurosci.* 14:Abstract 169.10 (1988)), cerebellum, thalamus, and cortical areas (Huettner, J. E. et al., *J. Neurosci.* 6:3044–3066 (1986)) were prepared as described below. Cultures were prepared on five 13 mm glass coverslips, each of which was coated with poly-L-lysine. Five days after plating, cultures were maintained for at least 10 days before infection with pHSVlac. Cultures contained approximately $1 \times 10^5$ cells per 35 mm dish at the time of pHSVlac infection.

EXAMPLE 2

Construction and Propagation of pHSVlac Stock pHSVlac was constructed using standard recombinant DNA techniques (Maniatis, T. et al., *Molecular Cloning,*

Cold Spring Harbor Laboratory Press, Cold Spring Harbor, N.Y.). The SV40 origin region and the 750 bp fragment flanked by Bam HI and Eco RI restriction sites were excised from the plasmid pCH110 (Hall, C. V. et al., *J. Molec. and App. Genet* 2:101–109 (1983)). The SV40 origin region was replaced with the HSV-1 c region nucleotides 47 to 1066 (McGeoch, D. J. et al., *Nucleic Acids Research* 14:1727–1745 (1986)) and the 750 bp fragment flanked by the Bam HI and Eco RI restriction sites was replaced with the a sequence (Davison, A. J. et al., *J. Gen. Virol.* 55:315–331 (1981)) nucleotides 127 to 1132 to yield the 8.1 kb plasmid pHSVlac.

The vector was packaged into an HSV-1 viral stock in the following manner: $1.5 \times 10^5$ CV1 monkey fibroblasts were seeded on a 60 mm plate, and incubated at 37° C. The following day, the cells were transfected (Graham, F. L. et al., *Virol.* 52:456–467 (1973)) with 0.5 ml of calcium phosphate co-precipitate containing 1 μg HSV-1 vector DNA and 9 μg salmon sperm DNA. Four hours later, the cells were shocked with 15% glycerol (Parker, B. A. et al., *J. Virol.* 31:360–369 (1979)). Following a 24 hour incubation at 37° C., $1.5 \times 10^6$ PFU of HSV-1 in 100 μl was added to each plate for 1 hour at room temperature. The virus inoculum was aspirated, and the plates were washed once with 5 ml of medium. Semiconfluent plates of CV1 cells which were not exposed to either virus or DNA were trypsinized. 5 ml of medium containing $5 \times 10^6$ recently trypsinized CV1 cells was added to complete the monolayer. Following incubation for 1.5 hours at 37° C., to allow the CV1 cells to attach to the plates, the medium was removed and replaced with either fresh liquid medium or methocel. After incubation for 3 days, virus was harvested or after incubation for 5 days, plaques were visualized with neutral red. Virus stocks were subsequently passaged at a 1:2 dilution on CV1 cells. This procedure will aid in propagating many different defective HSV-1 vectors, and in evaluating the properties of different strains and mutants of HSV-1 helper virus.

EXAMPLE 3

Recovery of pHSVlac from Neurons

An experiment was performed to demonstrate that pHSVlac DNA was present in cells two weeks after infection. It has been demonstrated that superinfection of a latently infected neuron results in a lytic infection; both the latent and superinfecting genomes are present in the progeny virus (Lewis, M. E. et al., *J. Gen. Virol.* 65:215 (1984)). Such an experiment was modified to investigate the question of whether pHSVlac could be recovered from previously infected cells.

To accomplish this goal, cultures (Hawrot, E. et al., *Methods Enzymol.* 58:574 (1979)) of dorsal root ganglia ($9 \times 10^4$ cells in 1.5 ml) were infected with 0.05 ml pHSVlac virus stock and incubated for two weeks at 37° C. Two weeks after infection with pHSVlac, cultures were infected with strain 17 ts K alone and incubated for two days at 31° C. in an effort to recover pHSVlac DNA in a HSV-1 virus stock.

Cultures were infected with $5 \times 10^5$ pfu of HSV-1 strain 17 ts K (Davison, M. J. et al., *J. Gen. Virol.*, 65:859 (1984)) and incubated for two days at 31° C. The resulting virus stock was passaged three times on $2 \times 10^6$ CV1 monkey fibroblasts at 31° C. to yield virus stocks DRG1 and DRG2. $1 \times 10^7$ CV1 cells were infected with $5 \times 10^7$ pfu of virus stock (DRG1, DRG2, ts K alone, or mock infected) and incubated at 31° C. for 24 hours.

DNA was analyzed as follows: $1 \times 10^7$ CV1 cells were infected with $5 \times 10^7$ pfu of pHSVlac virus stock and the cells were incubated at 31° C. for 24 hours. Total cellular DNA was prepared as described (Wigler, M. et al., *Cell* 16:777–785 (1979)) from CV1 cells, 5 μg of DNA was digested with 12.5 units of the restriction endonuclease Eco RI overnight at 37° C., resolved on 0.7% agarose gels, and transferred to Genetran as described (Southern, E. M., *J. Molec. Biol.* 98:503–517 (1975)). Hybridization and washing conditions were as described (Southern, E. M. *J. Molec. Biol.* 98:503–517 (1975)).

The probe was the 5.9 kb Eco RI fragment from the plasmid pCH110 (Hall, C. V. et al., *J. Molec. and App. Genet* 2:101–109 (1983)) radiolabeled with $^{32}P$ (Feinberg, A. P. et al., *Analytical Biochem.* 132:6–13 (1983)). This probe is homologous to pBR322 sequences and most of lacZ, lacking homology to the 133 bp at the 3' end. pHSVlac contains three Eco RI sites, one at each end of the pBR322 segment and a third in the lacZ gene 133 bp from the 3' end of the fragment. The 4.3 kb band contains most of the transcription unit in pHSVlac and the 2.3 kb band contains the pBR322 sequences. These two bands are present in equimolar amounts. A 1.5 kb fragment, which contains the 3' end of the lacZ gene, the SV-40 early region polyadenylation site, and the a sequence is not homologous to the probe. pHSVlac sequences are present in virus stocks containing the vector but are absent from virus stocks of ts K alone and from uninfected cells.

The presence of pHSVlac DNA was identified in this manner. The structure of pHSVlac DNA which persisted in sensory neurons for two weeks was found to be similar to the structure of pHSVlac DNA isolated from *E coli*. pHSVlac DNA was found to be absent from both a virus stock of strain 17 ts K alone and from mock infected cells. 1 to 10% of PC12 cells were β-galactosidase positive 24 hours after infection with virus stocks of pHSVlac recovered from neurons two weeks after infection. Thus pHSVlac DNA can persist, unaltered, in sensory neurons for at least two weeks and stably express β-galactosidase from the HSV-1 IE 4/5 promoter.

EXAMPLE 4

Expression of the LacZ Transcription Unit of pHSVlac in Mitotic Cells at the Restrictive Temperature of 37° C.

The fate of pHSVlac DNA in cells incubated at the restriction temperature of 37° C. was investigated. CV1 cells were infected with pHSVlac virus stock, and the cells were incubated at 37° C. Twenty-four hours after infection total cellular DNA was isolated and subjected to Southern analysis as described above. The results demonstrated that pHSVlac DNA is present in CV1 cells incubated for 24 hours at 37° C. Similar blots probed with an HSV-1 specific probe demonstrated that HSV-1DNA was also present in these cells.

The ability of pHSVlac to transcribe the lacZ transcription unit in pHSVlac was investigated. CV1 cells were infected with pHSVlac virus stock, and the cells were incubated for 24 hours at 37° C. Total cellular RNA was prepared (Chirgwin, J. M. et al., *Biochemistry* 18:5294–5299 (1979)), displayed on agarose gels, and the resulting Northern blots (Ecker, J. R. et al., *Proc. Natl. Acad. Sci. USA* 84:5202–5206

(1987)) were probed with a lacZ specific probe. A prominent band seen at 4.0 kb is the appropriate size for the correctly processed transcript from the lacZ transcription unit using the HSV-1 IE 4/5 promoter in pHSVlac. This 4 kb transcript is not present in cells infected with ts K alone nor in uninfected cells; therefore it must be derived from pHSVlac. Similar blots probed with a HSV-1 specific probe showed a pattern of bands indicative of expression of the HSV-1 IE genes in cells infected with pHSVlac and in cells infected with ts K alone but not in uninfected cells.

EXAMPLE 5

Expression of B-Galactosidase by pHSVlac

To determine if pHSVlac virus stock could infect neurons and express β-galactosidase, primary cultures of dissociated neurons were prepared (Hawrot, E. et al., *Methods Enzymol.* 58:574 (1979)), and the expression of β-galactosidase from pHSVlac in cells from dorsal root ganglia and superior cervical ganglia of newborn rats was studied.

The virus stock containing pHSVlac was prepared with HSV-1 strain 17 ts K (Davison, M. J. et al., *J. Gen. Virol.*, 65:859 (1984)) as helper virus. The titer of the virus stock was $1 \times 10^6$ pfu of strain 17 virus per ml and $8 \times 10^5$ infectious particles of pHSVlac per ml.

Cultures were infected with pHSVlac virus stock, then incubated for 24 hours at 37° C., fixed, and assayed for β-galactosidase activity in situ (Sanes, J. R. et al., *EMBO J.* 5:3133 (1986); Price, J. et al., *Proc. Natl. Acad. Sci. USA* 84:156 (1987)) using the chromogenic substrate, 5-bromo-4-chloro-3-indoyl β-D-galactoside (X-gal). Dissociated cell cultures (Hawrot, E. et al., *Methods Enzymol.* 58:574 (1979)) were prepared from newborn rat dorsal root ganglia (DRG) or superior cervical ganglia (SCG) and treated for 24 hours with $10^{-5}$M cytosine arabinoside. After 10 days in vitro, the cultures contained 3 to $8 \times 10^5$ cells per 35-mm plate; cultures were then infected with 0.1 ml of pHSVlac virus stock and incubated for 24 hours at 37° C. Cells were fixed with 0.5% glutaraldehyde and stained for beta-galactosidase activity with X-gal. The stained preparations were photographed and analyzed.

When infected at a multiplicity of infection (moi) of 0.1 to 0.4 (pHSVlac per cell) about 38% of the cells in the cultures of dorsal root ganglia and 11% of the cells in the cultures of superior cervical ganglia were β-galactosidase positive.

Experiments performed at higher ratios of pHSVlac virus to cells (moi=2) resulted in expression of β-galactosidase in virtually every cell. Cultures infected with HSV-1 strain 17 ts K alone or mock infected cultures contained less than 0.2% β-galactosidase positive cells.

Most of the β-galactosidase positive cells observed had the morphological characteristics of neurons. However, β-galactosidase positive cells which resembled glia were also observed.

These results demonstrate that the IE 4/5 promoter is capable of mediating constitutive gene expression in infected neurons. The expression of β-galactosidase was found to be independent of the moi of the ts K helper virus. A single particle of pHSVlac was sufficient to render a cell β-galactosidase positive. A productive lytic infection was not required in order to express the β-galactosidase gene.

EXAMPLE 6

Neuronal Infection of pHSVlac

To determine if some of the β-galactosidase positive cells identified in the experiments of Example 5 were indeed neurons, an experiment was performed to determine if β-galactosidase and a neuronal marker were present in the same cell. To do this, primary cultures of dorsal root ganglia (Hawrot, E. et al., *Methods Enzymol.* 58:574 (1979)) were infected with pHSVlac virus stock, incubated for 24 h at 37° C., fixed, and treated with a rabbit antiserum to β-galactosidase and mouse anti-rat monoclonal to one of two neuronal markers, either the A2B5 antigen (Eisenbarth, G. S. et al., *Proc. Natl. Acad. Sci. USA* 76:4913 (1979)) or the 150 and 180 kD subunits of neurofilament (Sternberger, L. A. et al., *Proc. Natl. Acad. Sci. USA* 80:6126 (1983)).

In detail, pHSVlac virus stock and cultures of dorsal root ganglia were prepared as described above except that cultures were prepared on 13-mm glass coverslips coated with 0.8 µg of laminin. Cultures ($5 \times 10^4$ cells in 0.5 ml) were infected with 0.1 ml of pHSVlac virus stock and incubated for 24 h at 37° C. Fixation with 4% paraformaldehyde in 0.1M $NaPO_4$ (pH 7.0) and immunohistochemistry was performed (Huettner, J. E. et al., *J. Neurosci.* 5:3044 (1986)) with a rabbit antibody to *E. coli* β-galactosidase (Cooper Biomedical, Malvern Pa.) diluted 1:800 and either mouse monoclonal to rat neurofilament (Sternberger, L. A. et al., *Proc. Natl. Acad. Sci. USA* 80:6126 (1983)) (SMI 33, Stenberer-Meyer) diluted 1:800 or mouse monoclonal A2B5 (Eisenbarth, G. S. et al., *Proc. Natl. Acad. Sci. USA* 76:4913 (1979)) supernatant diluted 1:2 as primary antibodies. Fluorescein isothiocyanate-conjugated goat $F(ab')_2$ antibody to mouse $F(ab')_2$ (Cooper Biomedical) diluted 1:200 and rhodamine isothiocyanate-conjugated goat $F(ab')_2$ antibody to rabbit $F(ab')_2$ diluted 1:250 (Cooper Biomedical) were used as secondary antibodies. Coverslips were mounted in PBS glycerol 1:1 containing 0.4% n-propyl gallate.

β-galactosidase-like immunoreactivity (β-gal-IR) was visualized with a rhodamine conjugated goat antibody to rabbit immunoglobulin G and A2B5 or neurofilament-like immunoreactivity (A2B5-IR or Nf-IR) was visualized with a fluorescein conjugated goat antibody to mouse immunoglobulin G.

Many of the same cells with neuronal morphology contained both A2B5-IR and β-gal-IR or Nf-IR and β-gal-IR. Parallel cultures treated with antibodies directed against either of the neuronal markers and rabbit preimmune serum followed by the fluorescent-conjugated antibodies contained either A2B5-IR or Nf-IR but no β-gal-IR. Cultures infected with ts K alone, or mock infected, and treated with antibodies against either neuronal marker and β-galactosidase contained either A2B5-IR or Nf-IR but no β-gal-IR. Thus, pHSVlac can infect rat sensory neurons and subsequently express β-galactosidase.

EXAMPLE 7

Expression in Neurons

Primary cultures were prepared from a variety of CNS areas, including spinal cord, cerebellum, thalamus, striatum, hippocampus, occipital cortex, temporal cortex, and frontal cortex. The cultures were grown for at least 10 days and treated with cytosine arabinoside to kill mitotic cells, thereby preventing glial cell overgrowth of the cultures. Cultures were then infected with pHSVlac, and after incubation at 37° C. for either 24 hours or 2 weeks, assays were performed to detect pHSVlac DNA and expression of *E. coli* β-galactosidase in neurons.

To demonstrate such expression, cultures were fixed and assayed for the co-localization of β-galactosidase-like immunoreactivity and neurofilament-like immunoreactivity using the immunofluorescent staining assay described above. Phase-positive cells from occipital cortex, temporal cortex and hippocampus demonstrated staining for both β-galactosidase-like and neurofilament-like immunoreactivity. In these cultures, between 60–70% of the neurons in microscopic fields examined were β-galactosidase positive. Some cells which contained β-galactosidase-like reactivity lacked neurofilament-like activity, and had the morphological appearance of glia, although further characterization of these cells was not made.

β-galactosidase-like reactivity was observed in cells which contained neurofilament-like reactivity in cultures of spinal cord, cerebellum, thalamus, striatum and frontal cortex. Sister cultures treated with pre-immune primary sera contained background levels of fluorescein and rhodamine fluorescence, and sister cultures treated with antibody against neurofilament antigens and rabbit pre-immune serum followed by the fluorescent-conjugated antibodies contained neurofilament-like immunoreactivity but did not contain β-galactosidase-like immunoreactivity.

Cultures infected with HSV strain 17 ts K alone, or mock infected, and treated with anti-neurofilament and anti-β-galactosidase antibodies followed by the fluorescent conjugated secondary antibodies, contained neurofilament-like immunoreactivity but did not contain β-galactosidase-like immunoreactivity. Phase-positive cells from the total neocortex and striatum demonstrated both neurofilament-like immunoreactivity and β-galactosidase-like immunoreactivity 2 weeks after infection with pHSVlac. Between 60–70% of striatal and neocortical neurons examined were β-galactosidase positive.

EXAMPLE 8

Persistence of pHSVlac and Stability of Expression

The persistence of pHSVlac, and the stability of its expression were investigated in cultured sensory neurons. Cultures of dorsal root ganglia (Hawrot, E. et al., *Methods Enzymol.* 58:574 (1979)) were infected with pHSVlac virus stock; following a two week incubation at 37° C., 49% of the cells were β-galactosidase positive as assayed with X-gal. Most of these cells had neuronal morphology. Cultures infected with HSV-1 strain ts K alone or mock infected contained less than 0.2% β-galactosidase positive cells.

The presence of β-galactosidase positive cells could have resulted from either stable persistence of pHSVlac in the same cell for two weeks or horizontal transmission of pHSVlac. If the presence of beta-galactosidase resulted from the stable persistence of pHSVlac, then the proportion of total cells expressing beta-galactosidase should have been approximately the same as the proportion of cells initially infected with the pHSVlac vector. In contrast, if horizontal transmission had occurred at a significant rate then all the cells would have contained pHSVlac DNA and would have expressed β-galactosidase, and both 17 ts K virus and pHSVlac virus would have been found in the culture medium.

Two weeks after infection, between 30–50% of the cells were found to be β-galactosidase negative, but neurofilament positive by immunofluorescence. Furthermore, two weeks after infection the amount of virus in the culture medium was either below detection (i.e. less than 10 plaque forming units (pfu) of strain 17 ts K per milliliter and less than 10 infectious particles of pHSVlac per milliliter), or very low (Table 1). The low level of virus observed might have been due to the release of virus from dead cells during the freezing and thawing of the preparation. In contrast, wt HSV-1 kills all cells in less than 24 hours.

Furthermore, in cultured peripheral nervous system neurons, as well as in cultures of differentiated PC-12 pheochromocytoma and differentiated N1E-115 mouse neuroblastoma cells, pHSVlac infection results in no detectable ts K or pHSVlac virus in the culture medium 2 weeks after infection. Thus, although it is not necessarily absent, the rate of horizontal transmission of pHSVlac is very low.

The experimental results show that the expression of beta-galactosidase resulted predominately, if not completely, from the persistence of the vector rather than its horizontal transmission.

TABLE 1

AMOUNT OF ts K AND pHSVlac VIRUS PRESENT IN MEDIUM FROM PRIMARY CULTURES OF NEOCORTEX TWO-WEEKS POST-INFECTION WITH pHSVlac

| Culture | ts K/ml+ | pHSVlac/ml* |
|---------|----------|-------------|
| 1 | $8 \times 10^2$ | $1 \times 10^1$ |
| 2 | $<10^1$ | $4 \times 10^1$ |
| 3 | $<10^1$ | $<10^1$ |
| 4 | $<10^1$ | $<10^1$ |

EXAMPLE 9

Differentiated Cell Culture $5 \times 10^5$ PC12 cells (Greene, L. A. et al., *Proc. Natl. Acad. Sci. USA* 73:2424–2428 (1976)) were seeded in 5 ml on 60 mm plates coated with 0.2 ml of 100 ug/ml collagen and 12 hours later nerve growth factor (NGF) was added to a final concentration of 10 ng/ml. $5 \times 10^5$ N1E-115 cells (Amano, T. et. al., *Proc. Natl. Acad. Sci. USA* 69:258–263 (1972); Garvican, J. H. et al., *Eur. J. Bicohem.* 76:251–261 (1977); Nelson, P. et al., *Proc. Natl. Acad. Sci. USA* 64:1004–1010 (1969)) were seeded in 5 ml on uncoated 60 mm plates and 12 hours later dibutyryl cyclic AMP (bt$_2$cAMP) was added to a final concentration of 1 mM. The cultures were fed with media containing the appropriate differentiating agent on day 2. On day 3 cultures were infected with $1 \times 10^5$ pfu of pHSVlac virus stock, and incubated for 24 hours or two weeks at 37° C. After the two week incubation, $1 \times 10^6$ CV1 cells were added to some N1E-115 cultures which were then incubated for an additional two days at 37° C. Cultures were then assayed for β-galactosidase activity in situ.

Alternatively, cultures were infected with $5 \times 10^5$ pfu of HSV-1 strain 17 ts K and incubated for two days at 31° C. The resulting virus stock was passaged three times on $2 \times 10^6$ CV1 monkey fibroblasts at 31° C. $1 \times 10^7$ CV1 cells were infected with $5 \times 10^7$ pfu of virus stock and incubated at 31° C. for 24 hours, and total cellular DNA was prepared (Wigler, M. et al., *Cell* 16:777–785 (1979)).

The structure of pHSVlac DNA and the helper virus DNA in the virus stock was examined. CV1 cells were infected with pHSVlac virus stock, and the cells were incubated at the permissive temperature of 31° C. Twenty-four hours after infection total cellular DNA was isolated (Wigler, M. et al., *Cell* 16:777–785 (1979)), and analyzed by Southern analysis as described above.

This experiment demonstrated that pHSVlac DNA is faithfully propagated in a HSV-1 virus stock using ts K as helper virus. Similar Souther blots were probed with a HSV-1 and pHSVlac specific probe. These blots demonstrated that the structure of the ts K grown in the presence of pHSVlac is similar to the structure of the ts K grown alone and that HSV-1 sequences are absent from uninfected cells. Furthermore, densitometry scanning of a band specific to pHSVlac and a band specific to ts K demonstrated that pHSVlac is present in roughly equimolar amount to ts K.

EXAMPLE 10

Infection of Non-Mitotic Cells with pHSVlac Results in Persistence of pHSVlac DNA and Stable Expression of β-Galactosidase As described above, pHSVlac can infect rat peripheral neurons and express β-galactosidase in a heterogeneous population of cells. For many types of experiments a homogenous population is required. Two non-mitotic cell culture systems; PC12 rat pheochromocytoma cells differentiated with NGF (Greene, L. A. et al., *Proc. Natl. Acad. Sci. USA* 73:2424–2428 (1976)) and N1E-115 adrenergic mouse neuroblastoma cells differentiated with bt2cAMP (Amano, T. et al., *Proc. Natl. Acad. Sci. USA* 69:258–263 (1972); Garvican, J. H. et al., *Eur. J. Bicohem.* 76:251–261 (1977); Nelson, P. et al., *Proc. Natl. Acad. Sci. USA* 64:1004–1010 (1969)); are homogenous populations of cells which closely resemble neurons. wt HSV-1 can infect PC12 cells (Rubenstein, R. et al., *J. Gen. Virol.* 64:2505–2509 (1983)) and ts K can infect and persist in differentiated N1E-115 cells (Gerdes, J. G. et al., *Virol.* 94:430–441 (1979)). PC12 and N1E-115 cells were differentiated with the appropriate agent for three days. Cultures were then infected with pHSVlac virus stock, incubated for 24 hours at 37° C., fixed with 0.5% glutaraldehyde, and assayed for β-galactosidase activity in situ, using X-gal (Price, J. et al., *Proc. Natl. Acad. Sci. USA* 84:156–160 (1987); Sanes, J. R. et al., *EMBO J.* 5:3111–3142 (1986)); 13% of the PC12 cells and 7% of the N1E-115 cells were β-galactosidase positive. The long processes in the β-galactosidase positive cells argue that mitosis had been arrested and differentiation had occurred before infection with pHSVlac. Differentiated PC12 cells and N1E-115 cells infected with ts K alone, or uninfected cells, contained less than 0.2% β-galactosidase positive cells.

To determine if pHSVlac can persist in non-mitotic cells, differentiated PC12 cells and N1E-115 cells were infected with pHSVlac virus stock, incubated for two weeks at 37° C., and assays were performed to detect pHSVlac DNA and expression of β-galactosidase. To demonstrate expression of β-galactosidase two weeks after infection with pHSVlac, cultures were fixed, and assayed for β-galactosidase activity using X-gal, (Price, J. et al., *Proc. Natl. Acad. Sci. USA* 84:156–160 (1987); Sanes, J. R. et al., *EMBO J.* 5:3111–3142 (1986)). Cultures infected with ts K alone or mock infected contained less than 0.2% β-galactosidase positive cells The ability of pHSVlac DNA to persist in non-mitotic PC12 and N1E-115 cells was investigated. It has been established that superinfection of a latently infected neuron results in a lytic infection and both the superinfecting genome and the latent genome are present in the progeny virus (Lewis, M. E. et al., *J. Gen. Virol.* 65:215–219 (1984)). Differentiated PC12 and N1E-115 cells were infected with pHSVlac virus stock and incubated for two weeks at 37° C. Cultures were then infected with ts K alone and incubated for two days at 31° C. Total cellular DNA was isolated (Wigler, M. et al., *Cell* 16:777–785 (1979)) from the resulting virus stocks, digested with the restriction endonuclease Eco RI, and Southern analysis (Southern, E. M. *J. Molec. Biol.* 98:503–517 (1975)) was performed to detect pHSVlac DNA as described above. The Southern blot revealed that pHSVlac DNA could faithfully persist in non-mitotic cells two weeks after infection but is absent from virus stocks of ts K alone and from uninfected cells. PC12 cells were infected with the pHSVlac virus stocks recovered from non-mitotic cells two weeks after infection, incubated from 24 hours at 37° C., fixed, and assayed for β-galactosidase activity with X-gal; 1% to 10% of the cells were β-galactosidase positive. In summary, three lines of evidence demonstrate that pHSVlac DNA can persist unaltered in non-mitotic cells for two weeks: First, the recovered pHSVlac DNA has a functional a sequence and HSV-1 origin of DNA replication since it was propagated in a HSV-1 virus stock; second, it has a functional transcription unit which expresses β-galactosidase in both non-mitotic cells two weeks after infection and in PC12 cells following recovery by superinfection; and third, the structure of pHSVlac DNA was unaltered as demonstrated by Southern analysis. Thus, pHSVlac can infect and persist in differentiated PC12 and N1E-115 cells, and stably express β-galactosidase for at least two weeks.

EXAMPLE 11

Infection with pHSVlac of a Wide Range of Mitotic Cell Types from Humans, Monkeys, and rodents Results in Expression of β-Galactosidase The ability of defective HSV-1 vectors to deliver genes into different mitotic cells types was investigated. A wide range of immortalized cell lines derived from humans, monkeys, and rodents were infected with pHSVlac and assayed for expression of β-galactosidase. The cell lines tested included monkey and mouse fibroblasts, adrenergic and cholinergic mouse neuroblastoma cells (Amano, T. et al., *Proc. Natl. Acad. Sci. USA* 69:258–263 (1972); Garvican, J. H. et al., *Eur. J. Bicohem.* 76:251–261 (1977); Nelson, P. et al., *Proc. Natl. Acad. Sci. USA* 64:1004–1010 (1969)), rat pheochromocytoma cells (Greene, L. A. et al., *Proc. Natl. Acad. Sci. USA* 73:2424–2428 (1976)), rat and mouse pituicytes (Kitagawa, S. et al., *Endocrinology* 120:2591– 2596 (1987); Herbert, E. et al., *Endocrinology* 102:218–226 (1978)), and a human neuroblastoma (Biedler, J. L. et al., *Cancer Research* 38:3751–3757 (1978)). Cultures were infected with pHSVlac virus stock, incubated for 24 hours at 37° C., and the amount of β-galactosidase activity was determined by a quantitative solution assay using ONPG. Parallel cultures were fixed, assayed for β-galactosidase activity in situ using the chromogenic substrate X-gal, and the percentage of β-galactosidase positive cells was determined. The ratio of β-galactosidase activity in cultures infected with pHSVlac and ts K was evaluated. This ratio was normalized to a per cell infected with pHSVlac basis using the results from the in situ assay. As shown in Table 2, high levels of β-galactosidase activity were observed in every cell line tested. There was a five fold variation in β-galactosidase levels among the cell lines tested. In CV1 cells 24 hours after infection with pHSVlac the β-galactosidase specific activity was 115 nmoles ONPG cleaved/min/mg protein. Thus, it may be concluded that HSV-1 vectors should be useful for transferring genes into a wide range of mitotic mammalian cell lines, including those derived from humans.

TABLE 2

β-GALACTOSIDASE ACTIVITY PER
INFECTED CELL IN VARIOUS CELL LINES 24
HOURS AFTER INFECTION WITH pHSVLAC VIRUS

| Cell Line | $A_{420}$ pHSVlac/ts K |
|---|---|
| CV1 Monkey Fibroblast | 264 |
| LM tk⁻ Mouse Fibroblast | 59 |
| N1E-115 Mouse Adrenergic Neuroblastoma | 85 |
| NS-20Y Mouse Cholinergic Neuroblastoma | 65 |
| PC12 Rat Pheochromocytoma | 156 |
| AtT-20 Mouse Pituicyte | 65 |
| GH4 Rat Pituicyte | 78 |
| SK-N-BE(2) Human Neuroblastoma | 52 |

$1 \times 10^6$ cells were infected at a multiplicity of 0.1 with pHSVlac virus stock, or with ts K alone. The cells were incubated for 24 hours at 37° C. β-galactosidase activity per cell infected with pHSVlac was determined as described in Experimental Procedures. Each measurement is the average of three separate cultures from at least two separate experiments whose values differed by less than 10%.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. The recombinant HSV-1 vector pHSVlac.

2. The vector of claim 1, wherein said vector further comprises an inserted gene sequence, and wherein said vector infects a non-mitotic cell.

3. The vector of claim 2, wherein a gene product of said inserted gene sequence alters the physiology of said non-mitotic cell.

4. The vector of claim 2, wherein said inserted gene sequence is associated with disease.

5. The vector of claim 2, wherein said inserted gene sequence encodes at least one member selected from the group consisting of a neural protein, a histological marker, a growth factor, an oncogenic protein, and a toxic peptide.

6. The vector of claim 4, wherein said disease is selected from the group consisting of lysosomal storage disease, Lesch-Nyhan syndrome, amyloid polyneuropathy, Alzheimer amyloid, retinoblastoma, and Duchenne's muscular dystrophy.

7. The recombinant HSV-1 vector pHSVlac, said vector having an *E. coli* lacZ gene, wherein, said *E. coli* lacZ gene contained in said vector has been deleted and replaced with a foreign gene sequence, and wherein said vector infects a non-mitotic cell.

8. The vector of claim 7, wherein a gene product of said foreign gene sequence alters the physiology of said non-mitotic cell.

9. The vector of claim 7, wherein said foreign gene sequence is associated with disease.

10. The vector of claim 9, wherein said disease is selected from the group consisting of lysosomal storage disease, Lesch-Nyhan syndrome, amyloid polyneuropathy, Alzheimer amyloid, retinoblastoma, and Duchenne's muscular dystrophy.

11. The vector of any one of claims 1, 2, 4, 5, 7, and 9, wherein said vector is packaged with an HSV-1 mutant helper virus having a temperature sensitive mutation in an immediate early 3 (IE3) gene.

12. The recombinant HSV-1 vector pHSVlac, said vector having a beta-lactamase gene sequence of pBR322, wherein, said beta-lactamase gene sequence contained in said vector is replaced with a different gene sequence that is a reporter gene sequence or a selectable marker gene sequence sufficient to permit the recognition or selection of said pHSVlac vector containing the replaced beta-lactamase gene.

13. The recombinant HSV-1 vector pHSVlac, said vector having an HSV-1 IE 4/5 promoter sequence, wherein, said HSV-1 IE 4/5 promoter sequence contained in said vector is replaced with another promoter sequence sufficient to direct the transcription of a sequence operably linked to said other promoter.

* * * * *